(12) United States Patent
Noel et al.

(10) Patent No.: US 12,303,176 B2
(45) Date of Patent: May 20, 2025

(54) STRAPPING DEVICE FOR STABILISING A PERIPROSTHETIC FRACTURE

(71) Applicant: COUSIN BIOTECH, Wervicq-Sud (FR)

(72) Inventors: Stéphane Noel, Hantay (FR); Safa Ouerghemmi, Mons en Baroeul (FR)

( * ) Notice: Subject to any disclaimer, the term of this patent is extended or adjusted under 35 U.S.C. 154(b) by 413 days.

(21) Appl. No.: 17/763,247

(22) PCT Filed: Sep. 22, 2020

(86) PCT No.: PCT/EP2020/076426
§ 371 (c)(1),
(2) Date: Mar. 24, 2022

(87) PCT Pub. No.: WO2021/058477
PCT Pub. Date: Apr. 1, 2021

(65) Prior Publication Data
US 2022/0354554 A1 Nov. 10, 2022

(30) Foreign Application Priority Data
Sep. 24, 2019 (FR) ...................................... 19 10501

(51) Int. Cl.
*A61B 17/82* (2006.01)
(52) U.S. Cl.
CPC ..................................... *A61B 17/82* (2013.01)
(58) Field of Classification Search
CPC ....................................................... A61B 17/82
See application file for complete search history.

(56) References Cited

U.S. PATENT DOCUMENTS

| | | | | |
|---|---|---|---|---|
| 2,987,062 A | * | 6/1961 | Ellison | A61B 17/82 606/77 |
| 4,889,110 A | * | 12/1989 | Galline | A61B 17/2812 403/396 |
| 5,330,489 A | * | 7/1994 | Green | A61B 17/82 606/151 |

(Continued)

FOREIGN PATENT DOCUMENTS

| | | |
|---|---|---|
| EP | 2455001 A2 | 5/2012 |
| WO | 2018/111275 A1 | 6/2018 |

OTHER PUBLICATIONS

I. Peeters, A. Depover, A. Van Tongel, L. De Wilde A review of metallic and non-metallic cerclage in orthopaedic surgery: Is there still a place for metallic cerclage? Injury, vol. 0, No. 0 Jul. 2019.

*Primary Examiner* — David W Bates
(74) *Attorney, Agent, or Firm* — Cabinet Beau de Lomenie (57) ABSTRACT

The present disclosure relates to an implantable strapping device comprising an elongate hollow textile element comprising an attachment portion and an adjustable loop, the perimeter of the adjustable loop is adjustable by sliding a portion of the adjustable loop in an interior volume of a sleeve arranged in the textile element, and a strapping closing member comprising a front part with which the adjustable loop or the attachment portion is connected, and a rear part comprising a first U-shaped housing configured to receive part of the attachment portion or of the adjustable loop. The strapping device thus comprises a clamping position of the strapping by sliding the adjustable loop in the sleeve, and a locking position in which the sliding of the adjustable loop is prevented by the sleeve.

20 Claims, 5 Drawing Sheets

(56) References Cited

U.S. PATENT DOCUMENTS

| | | | | |
|---|---|---|---|---|
| 5,540,703 A * | 7/1996 | Barker, Jr. | A61L 17/04 | 606/139 |
| 5,569,253 A * | 10/1996 | Farris | A61B 17/8861 | 606/103 |
| 5,573,286 A * | 11/1996 | Rogozinski | D04G 5/00 | 606/228 |
| 5,693,060 A * | 12/1997 | Martin | A61B 17/12013 | 606/148 |
| 6,605,091 B1 * | 8/2003 | Iwanski | A61B 17/82 | 606/74 |
| 6,626,944 B1 * | 9/2003 | Taylor | A61B 17/82 | 623/17.11 |
| 10,076,375 B1 * | 9/2018 | Martel | A61B 17/82 | |
| 2002/0040222 A1 * | 4/2002 | Hashimoto | A61B 17/7022 | 606/330 |
| 2006/0276896 A1 * | 12/2006 | Fallin | A61B 17/82 | 623/908 |
| 2007/0100345 A1 * | 5/2007 | Fernandez | A61B 17/82 | 606/74 |
| 2008/0234679 A1 * | 9/2008 | Sarin | A61B 17/82 | 606/103 |
| 2010/0211075 A1 * | 8/2010 | Stone | A61B 17/683 | 606/281 |
| 2010/0298828 A1 * | 11/2010 | Chico Roca | A61B 17/688 | 606/70 |
| 2011/0224799 A1 * | 9/2011 | Stone | A61B 17/842 | 623/23.26 |
| 2012/0059418 A1 * | 3/2012 | Denham | A61B 17/8869 | 606/232 |
| 2012/0089193 A1 * | 4/2012 | Stone | A61B 17/8685 | 606/301 |
| 2012/0215224 A1 * | 8/2012 | Songer | A61B 17/82 | 606/74 |
| 2013/0079778 A1 * | 3/2013 | Azuero | A61F 2/0811 | 606/74 |
| 2013/0144338 A1 * | 6/2013 | Stone | A61B 17/0401 | 606/232 |
| 2013/0317287 A1 * | 11/2013 | Noel | A61F 2/0022 | 600/37 |
| 2014/0378977 A1 * | 12/2014 | Russi | A61B 17/151 | 606/1 |
| 2015/0297274 A1 * | 10/2015 | Dreyfuss | A61B 17/0487 | 606/74 |
| 2016/0183991 A1 * | 6/2016 | Pratt | A61B 17/82 | 606/74 |
| 2017/0265917 A1 * | 9/2017 | Dreyfuss | A61B 17/8861 | |
| 2018/0161083 A1 * | 6/2018 | Kobayashi | A61B 17/809 | |
| 2018/0256227 A1 | 9/2018 | Maxson | | |

* cited by examiner

STRAPPING DEVICE FOR STABILISING A PERIPROSTHETIC FRACTURE

TECHNICAL FIELD

The present invention relates to a strapping device, in particular for the consolidation of a periprosthetic fracture.

BACKGROUND

Bone fractures are mainly caused by trauma (falls, shocks, road accidents, etc.). There are, however, other causes of bone fracture, such as periprosthetic fractures. By definition, a periprosthetic fracture occurs at the level of a bone located around or in the vicinity of a prosthetic implant. The periprosthetic fractures in total hip arthroplasty represent a frequent problem in orthopaedic surgery. For example, the periprosthetic fractures of the femur occur in 0.1% to 6% of patients who have undergone total hip arthroplasty.

Periprosthetic fractures can occur during implantation of the prosthetic implant intraoperatively or more frequently, after intervention, during trauma. They can also occur after the intervention postoperatively. In this case, a review is necessary. The review of periprosthetic fractures of the femur is the third cause of surgical review just after the aseptic loss and the infection (cf "*A review of metallic and non-metallic cerclage in orthopaedic surgery: Is there still a place for metallic cerclage?*", *Injury*, volume 0, No. 0 July 2019, I. Peeters, A. Depover, A. Van Tongel, L. De Wilde).

The treatment of a fracture has the function of consolidating one or several bones or restoring joint functions.

For this purpose, it is necessary to maintain the bone or the assembly of bone fragments to create a stable environment conducive to healing. This treatment is carried out using osteosynthesis plates, screws and cables and/or wires using a technique called strapping. The therapeutic decision to treat the fracture will be made according to the location of the fracture and to the type of fracture. The strapping has many applications in orthopaedics as a fixation method. The traumatic strapping can be considered as an osteosynthesis strapping used mainly for the consolidation of a periprosthetic fracture. When the implant is stable, it is the ideal solution. The traumatic strapping can be installed on the elderly subjects, sportsmen but also young subjects. This implantable strapping has the function of restoring the joint function of the affected limb by means of an osteosynthesis plate which is an open or closed assembly of the fragments of a fractured bone. The strapping indications are numerous and can be chosen in particular by the following indications, cited without limitation: a prophylactic strapping in total joint prostheses, following intraoperative femoral fractures, following unstable intertrochanteric fractures possibly associated with an intramedullary nailing, following acetabular fractures, periprosthetic femoral fractures, in the context of a total hip arthroplasty review, following complications resulting from a total shoulder arthroplasty, or following periprosthetic elbow fractures. Today, there are two main families of strappings: those comprising a metallic strapping wire and those comprising a non-metallic strapping wire. The strappings called metallic strappings are the oldest used strappings and can comprise one or several wires made of stainless steel or titanium or based on other alloys such as a cobalt and chromium alloy. They generally comprise metallic wires in braided or twisted monofilament or multifilament form. The metallic strapping wire is disposed around the bone assembly to be treated in the form of one or several loops then the ends of the wire are held together either by twisting the ends together in the form of a twist or using a complementary metallic piece acting as a clasp and pinching the two ends of the wire together.

Non-metallic strappings can comprise one or several wires in a non-absorbable synthetic polymer in the form of a multi-filament stranded braid. Non-metallic strappings are known in which the braid forms one or several loops around the bone assembly to be treated and the loops are held around said assembly using a knot made on the free ends of the braid. These strappings do not comprise a member for closing the strapping, or means for tensioning and therefore gradually clamping the strapping. These strappings are generally based on non-absorbable suture wires.

Other strappings with a closing system are known, such as the strapping marketed under the brand SuperCable® from KINAMED comprising a cable formed of a nylon core surrounded by a braided fiber sheath made of ultra-high molecular weight polyethylene and of a nylon closing system.

A similar strapping system is also known marketed under the brand ORTHOLOX POLYMER® by the company ORTHOLOG or marketed under the brand NESPLON® by the company ALFRESA. These last two strappings are in the form of a flat braid and comprise ultra-high molecular weight polyethylene.

The strapping of the company ORTHOLOG has a titanium blocking member, whereas the strapping marketed by ALFRESA closes with a simple knot.

The bone assembly or the bone held by the strapping wire must undergo traction concomitant with torsion to remain in its implantation position. The traction is carried out using a strapping for tensioning the tie. The tension of the strapping must be maintained throughout the bone fusion process in order to avoid movement between the bone fragments. By way of example, the strapping marketed by the company KINAMED and comprising a 1.5 mm braid mixing ultra-high molecular weight polyethylene and polyamide 6-6, with a recommended applied tensile strength of 530 Newton, presents a tension loss of approximately 46% during the clamping of the braid. In addition to the tension, the strapping must also maintain sufficient compression on the bone to ensure the osteosynthesis. However, the metallic strappings have limited elastic deformation, which compromises their ability to maintain compression on the bone fragments held together.

Non-metallic strappings have the advantage of having a high elastic spring-back, which represents a favorable mechanical behavior allowing a margin of displacement between the bone fragments in which the compression between the bone fragments can be maintained. Metallic strappings also have the disadvantage of presenting in some cases problems of irritation, damage or being likely to break and in this case release metal debris into the body. The rupture of the metallic strappings also exposes the medical staff (surgeons, nurses, technicians) to a high risk of infection.

The rupture of a metallic cable can also cause an interruption in the flow of blood to the bone. Non-metallic strappings, particularly made of polymer material, have the advantage of eliminating these risks.

Non-metallic strappings nevertheless have the disadvantage that their two free ends cannot be closed by being twisted together, as it is the case for metallic strappings. Indeed, it is necessary either to make a knot on their ends which can cause a loss of tension depending on the clamping carried out or a shearing effect, or to use a metallic closing member.

The metallic closing members complicate the surgical technique since once the strapping tie has passed at least once around the assembly of bone fragments to be treated, it is necessary to introduce the end of the tie into the closing member which requires extra attention from the surgeon.

In addition, when the strapping tie forms several superimposed strapping loops, these must be parallel to each other and must not be superimposed/overlap over the entire circumference of the strapping. However, it can be difficult to visualize the correct positioning of the strapping loops, particularly for the portions of the loops disposed behind the bone. If the tie is improperly positioned, or moves, the compression exerted on the bone assembly or the bone to be treated will not be homogeneous, and the resulting bone repair will be incomplete. This positioning step is restrictive and lengthens the surgical time. This disadvantage is increased tenfold when it is necessary to place several ties to form separate strappings. Once the strapping tie has passed through the closing member, the tie is tensioned using a tensioner which is generally specific to the supplier of the strapping. When the strapping tie is clamped at the correct tension, the ends of the tie are secured by means of a closing member. This closing member can for example comprise a valve which presses on the ends of the strapping tie. There are also closing members comprising a screw clamping system which can cause abrasion of the tie of the strapping which is in a non-metallic material.

The surgeon may also need to maintain preliminary, that is to say temporary, tension on a given strapping in order to place other strapping devices, and then return to the first strapping in order to adjust its tension. It may indeed be necessary when the osteosynthesis strapping comprises several strapping devices to be able to gradually clamp them.

Metallic cables have the disadvantage that once they are crimped, that is to say once their free ends are twisted on themselves, it is not possible to correct the clamping tension. It has thus been designed for metallic strappings, a strapping for maintaining the intermediate clamping tension before crimping together the ends of the metallic tie in a definitive manner. This strapping comprises a piece included in the tensioner and marketed, for example, by the company Synthes, which can be separated from the tensioner to hold in position the metallic strapping tie while placing another metallic strapping tie. This technique has the disadvantage of involving the presence of an additional instrument, in addition to the tensioning instrument and to the closing member, to be managed during the intervention for the surgeon, and to be stored and sterilized for the hospital. Moreover, this intermediate tensioning system may clutter up the surgical site, which can be narrow because of the presence of soft tissues.

There is therefore a need for strapping devices requiring as few instruments as possible for their final and/or intermediate tensioning, and limiting the number of operations for their installation.

SUMMARY

The present disclosure thus relates to a strapping device facilitating the surgical procedure, and making it possible to save time in order to avoid/limit the risk of infection.

The present disclosure also relates to a strapping device that performs the clamping of the strapping gradually, and ensures an intermediate and/or final tension without the need for an intermediate piece for maintaining an intermediate clamping tension.

The present disclosure relates to a strapping device that allows a minimally invasive surgical technique to limit the post-operative pain and particularly that does not require the use of a strapping for maintaining the intermediate clamping different from the tensioner.

The present disclosure thus relates, according to a first aspect, to an implantable strapping, particularly for the consolidation of a periprosthetic fracture, comprising:
  an elongate hollow textile element comprising an attachment portion and an adjustable loop, a perimeter of the elongate hollow textile element is adjustable by sliding a portion of the adjustable loop in an interior volume of a sleeve arranged in the textile element, and
  a strapping closing member comprising:
    a front part with which the adjustable loop or the attachment portion is connected, and
    a rear part comprising a first U-shaped housing configured to receive part of the attachment portion or of the adjustable loop, and
  the strapping device further comprises:
    a clamping position of the strapping, in which traction on a free end A of the elongate element in a first direction causes the sliding of the adjustable loop portion in the interior volume of the sleeve and correlatively the reduction in the perimeter of the adjustable loop, and
    a locking position in which the sliding of the adjustable loop is prevented when traction is exerted on the adjustable loop in a second direction, opposite to the first direction.

Advantageously, the elongate textile element is passed around a bone or an assembly of bone fragments to be treated in order to encircle it so as to form a strapping loop. This strapping loop thus comprises, over its length, a part corresponding to the adjustable loop, the sleeve then the attachment portion. The adjustable loop is closed by means of the strapping closing member in connection with the adjustable loop on the one hand, and the attachment portion on the other hand.

Part of the length of the strapping loop is therefore adjustable by sliding a portion of the adjustable loop inside the sleeve by exerting traction on the free end in a first direction. When traction is exerted in a second direction opposite to the first direction, the sleeve blocks the sliding of the adjustable loop. It is therefore not necessary to use an intermediate clamping piece, the elongate element being configured to block the clamping of the adjustable loop.

The length of the sleeve, its inner diameter and its tribological properties, in particular linked to its relief textile structure, are determined so as to create an engagement area between the outer surface of the part of the elongate element and the inner surface of the sleeve.

Preferably, the sleeve is delimited between inlet and outlet orifices of the elongate element in the interior volume of the sleeve.

Preferably, the sleeve is a member for locking and unlocking the sliding of the adjustable loop portion disposed in its interior volume.

In the clamping position of the strapping, the inlet and outlet orifices of the sleeve tend to get closer or to remain apart along a distance Is close to the initial distance separating the inlet and outlet orifices of the sleeve at rest, so that the sleeve authorizes the sliding of the adjustable loop portion therein.

In the locking position, the inlet and outlet orifices of the sleeve tend to move apart along a distance, greater than the initial distance separating the inlet and outlet orifices of the sleeve at rest, so that the inner diameter of the sleeve in the locked state is smaller than the inner diameter of the sleeve at rest. The portion of the adjustable loop is thus clamped by the sleeve and blocked by the latter.

Advantageously, this intermediate and/or final clamping is reversible. It suffices to exert traction on a portion of the adjustable loop in the direction while holding the sleeve to authorize its sliding in the clamping sleeve.

Preferably, the U-shaped housing behaves like a hook receiving part of the length of the elongate element to close the strapping.

In a first example, the U-shaped housing comprises an introduction area (for the introduction of part of the elongate element into the U-shaped housing) and a receiving area (for the receipt of part of the elongate element in the U-shaped housing) formed substantially in the groove of the U-shaped housing, said introduction and receiving areas are dimensioned relative to the size of the part of the elongate element so that the placement of the part in the receiving area is obtained by the deformation of the part during its passage in the introduction area.

Particularly, the introduction area has a width smaller than the space requirement (in particular the outer diameter of the elongate element) of the part of the attachment portion or of the adjustable loop, and the receiving area has a width or a diameter (when it is rounded) greater than or equal to the diameter or the space requirement of the part.

Preferably, the U-shaped housing comprises side walls substantially facing each other, as well as a receiving area formed substantially in the groove of the U-shaped housing, and an introduction area. The distance separating the side walls in the introduction area is smaller than the distance separating the side walls in the receiving area.

Particularly, the introduction area is smaller than the outer diameter of the elongate element, and/or the distance separating the side walls in the receiving area is greater than or equal to the outer diameter of the elongate element.

This disposition allows retaining said adjustable loop part or the attachment portion part in the groove of the U-shaped housing.

In another example, the distance separating the side walls in the introduction area and the distance separating the side walls in the receiving area can be similar, or in a ratio of the distance separating the side walls in the introduction area over the distance separating the side walls in the receiving area between [0.7; 1], upper and lower bounds inclusive.

The front part is configured to be connected with the adjustable loop or the attachment portion. The front part can thus comprise a through opening in which the adjustable loop or the attachment portion is passed for its securing, in particular mechanical securing, to the front part.

The part of the adjustable loop or of the attachment portion placed in the hollow of the U-shaped housing can thus be manually removed therefrom, then replaced, as many times as necessary.

The tension exerted in operation on the strapping and the recessed shape of the housing are sufficient to maintain the part of the adjustable loop or of the attachment portion in the hollow of the U-shaped housing, and therefore secured thereto.

The elongate hollow textile element can be chosen among a tubular braid, a tubular knit or any other tubular textile element having an equivalent behavior. Preferably, the best results in terms of locking and unlocking of the sleeve have been obtained when the elongate element is a hollow tubular braid.

The elongate hollow textile element may comprise one or several fiber spun yarn(s) and/or one or several multifilament yarn(s) and/or one or several monofilament yarn(s).

The yarn(s) can comprise/be made of absorbable and/or non-absorbable and/or synthetic material.

The elongate hollow textile element preferably comprises a first free end A and a second free end B.

The fiber spun yarn(s) and/or multifilament yarn(s) and/or monofilament yarn(s) is/are made of one or several material(s), preferably chosen from the list comprising: polyolefins, particularly UHMWPE polyethylenes (ultra-high molecular weight polyethylene), in particular of DYNEEMA® brand or of SPECTRA® brand, or polypropylene; polytetrafluoroethylene (PTFE);

polyamides, particularly polyamide 6 or polyamide 6-6; polyesters, particularly polyethylene terephthalate; polyetheretherketone (PEEK), or a mixture thereof.

The yarns are preferably made of one or several non-absorbable material(s), such as those mentioned above.

The strapping closing member is made of a rigid or semi-rigid material. Preferably, the sleeve is disposed (in particular over the length of the elongate element) between the adjustable loop and the attachment portion. Preferably, the outer diameter of the elongate textile element is greater than 0 mm and less than or equal to 20 mm, more preferably between 0.5 mm and 3 mm (upper and lower bounds inclusive).

Preferably, the distance between the inlet and outlet orifices of the sleeve is greater than 10 mm and less than or equal to 100 mm, more preferably greater than or equal to 15 mm and less than or equal to 35 mm, in particular ranging from 25 mm to +/−5 mm.

Preferably, the adjustable loop has a length, measured over the length of the elongate element, greater than or equal to 10 mm and less than or equal to 200 mm, more preferably greater than or equal to 50 mm and less than or equal to 150 mm, in particular ranging from 100 mm to +/−20 mm. Preferably, the elongate element has a total length greater than or equal to 40 mm, and less than or equal to 500 mm, more preferably ranging from 170 mm to +/−50 mm.

Preferably, the attachment portion, in particular the attachment loop, has a length, measured over the length of the elongate textile element, greater than or equal to 100 and less than or equal to 50 mm, in particular ranging from 20 mm to +/−5 mm.

Preferably, the strapping closing member is made of an alloy comprising at least stainless steel and/or titanium and/or titanium/nickel and/or cobalt/chromium.

In a first example, the blocking member comprises a first auxiliary branch and a main branch at least partly delimiting the first U-shaped housing.

Preferably, the first auxiliary branch comprises an inner side wall and the main branch comprises a first inner side wall, which at least partly delimit said (first) U-shaped housing (and into which said side walls project).

Preferably, the width of the main branch measured along its upper face is greater than the width of the auxiliary branch measured along its upper face.

Preferably, the auxiliary branch forms an angle alpha with the main branch, less than or equal to 45°, in particular less than or equal to 30°.

The angle alpha is preferably measured as being the angle (measured in absolute value) formed between a first longitudinal axis and a second longitudinal axis of the main branch (extending between the front and rear parts).

The definitions and various aspects described with reference to the housing, or first housing in the present text also apply, alone or in combination, to the second and/or third and/or fourth housing(s) described in the present disclosure.

The first housing can also be designated by the term housing in the present disclosure.

In a second example, the adjustable loop, or the attachment portion being a loop, is configured to be passed around the main branch.

Preferably, part of the adjustable loop or part of the attachment loop is disposed in the receiving area formed substantially in the groove of the (first) U-shaped housing.

In a third example, in the locking position, the sliding of the adjustable loop is prevented by the sleeve.

In a fourth example, the strapping closing member comprises a second U-shaped housing configured to receive part of the attachment portion or of the adjustable loop.

Particularly, the second U-shaped housing is partly delimited by the main branch. Thus, when part of the adjustable loop or of the attachment portion, in particular an attachment loop, is disposed around the main branch, it is received in the first and second housings, which improves the holding of the elongate element in the strapping closing member.

In a fifth example, the strapping closing member comprises a second auxiliary branch, and the main branch and the second auxiliary branch partly delimit the second housing.

Preferably, the second auxiliary branch comprises an inner side wall and the main branch comprises a second inner side wall, which are disposed facing each other and open out into said second housing.

In a sixth example, the rear part or the front part comprises the second housing.

The blocking member comprises a longitudinal axis passing through the main branch, and particularly a transverse axis, substantially perpendicular to the longitudinal axis (in particular separating the front part from the rear part).

The first and second housings can be disposed on either side of the longitudinal axis, in the front part and/or the rear part or on the same side of the longitudinal axis, both in the front part and in the rear part.

When the front part comprises the second housing, part of the adjustable loop or of the attachment portion is disposed in the hollow of the second housing, and thus allows its connection with the front part of the closing member.

In a seventh example the front part or the rear part comprises a third U-shaped housing, and optionally a fourth U-shaped housing.

The third and/or fourth U-shaped housing(s) is/are each at least partly delimited by an auxiliary branch and said main branch.

Preferably, and generally, the strapping closing member comprises a main branch, as described in the present disclosure, from which one or several auxiliary branches, as described in the present disclosure, project(s) and with which it/they at least partly delimit(s) said first and/or second and/or third and/or fourth U-shaped housing(s).

In an eighth example, the front part of the strapping closing member and optionally the rear part of the strapping closing member has/each have the general shape of an anchor.

Preferably, the anchor comprises a rounded external edge.

Preferably, the anchor comprises one U-shaped housing or two U-shaped housings.

In a ninth example, the strapping device comprises an annular member, the free end of the elongate element being configured to pass through the annular member, and the annular member is at least partly formed in the elongate hollow textile element.

This annular member, like an eyelet, allows protecting in shear the elongate textile element in the strapping position. The free end therefore also slides through the annular member.

The annular member thus comprises a central empty space through which the free end is passed.

Preferably, the diameter of the annular member is fixed (and therefore not adjustable).

When the strapping device according to the disclosure is implanted, and therefore forms a strapping around at least one bone, traction is exerted on the free end in the first direction to obtain the sliding of the portion of the loop adjustable in the sleeve, the free end also slides inside the intra-annular empty space of the annular member, the shear stress exerted by the elongate element on the sleeve, particularly on the outlet orifice of the sleeve, is thus advantageously transferred to the annular member. The free end therefore does not exert a shear force directly on the sleeve during the clamping.

This disposition allows improving the force at break (daN) of the elongate element and therefore increasing the tensile force which can be exerted for the clamping of the adjustable loop.

In a tenth example, the annular member comprises a free end of the elongate element passed through at least one portion of said elongate element so as to form a loop.

Preferably, the annular member is formed by passage of the free end (that is to say the second free end of the elongate element) of the elongate element through at least two wall portions of the elongate element by passing through its interior volume, said wall portions being substantially opposite (that is to say facing each other). Said wall portions are preferably in the vicinity of the second free end and/or disposed between the second free end and the attachment portion (or attachment loop).

In an eleventh example, the annular member is secured to a portion of the elongate element disposed between, and in the extension of, the sleeve and the attachment portion.

Preferably, the second free end once passed through the elongate element is secured to a securing portion of the elongate element, for example by forming a splice. Said splice comprising yarns from the second free end and yarns from the securing portion.

The securing portion, particularly comprising a portion of the length of the elongate element, can also be passed through the second free end, then the second free end is secured to the securing portion, for example using a splice, in particular as described above.

In a twelfth example, at least one of the housings chosen among: the first, second, third and fourth housings, comprises at least one side wall comprising one or several projections, in particular one tooth or several teeth, projecting into said housing.

Particularly, the inner side wall of an auxiliary branch or the inner side walls of the auxiliary branches and/or the first inner side wall and/or the second inner side wall of the main branch, comprises/each comprise projections.

These projections come into contact with part of the adjustable loop and/or the attachment portion.

In a thirteenth example, the front part comprises a through opening, particularly disposed in the main branch, and through which the adjustable loop or the attachment portion is passed.

This disposition allows securing the adjustable loop or the attachment portion to the front part of the strapping closing member.

The attachment portion, passed through the through opening, can comprise a knot at its end forming an abutment against the through opening.

In a fourteenth example, the through opening extends between and opens out onto two side walls of the main branch.

The through opening opens out particularly onto the first and second inner side walls of the main branch.

In a fifteenth example, the through opening extends between and opens out onto upper and lower walls of the main branch.

In a sixteenth example, the closing member comprises an anchoring stud and the attachment portion is anchored to the anchoring stud, in particular the attachment loop.

Preferably, the attachment loop is passed around the anchorage stud.

Said stud preferably projects from the upper wall or from the lower wall of the main branch.

In a seventeenth example, the elongate hollow textile element is a braid, particularly comprising one or several multifilament yarns.

The examples from one to seventeen according to the disclosure can be combined together, independently of each other.

The present disclosure relates, according to a second aspect, to an implantable osteosynthesis strapping device, in particular for the consolidation of a periprosthetic fracture, comprising a strapping according to any one of the variants with reference to the first aspect of the disclosure, in particular from one to seventeen cited above. The osteosynthesis strapping device further comprises a reinforcing plate and at least one strapping for securing said reinforcing plate, configured to allow the securing of the plate to at least one bone portion.

The securing strapping device can be any type of implantable strapping device suitable for the securing of a plate to at least one bone element, for example screws.

The present disclosure relates, according to a third aspect, to a kit for the use of an osteosynthesis strapping device, in particular for the consolidation of a periprosthetic fracture, comprising an osteosynthesis strapping device according to the second aspect of the invention or an implantable strapping device according to any one of the examples described according to a first aspect or a fifth aspect, and a tensioner, particularly a non-implantable tensioner.

The free end of the elongate element and/or any other part of the elongate element can be tensioned using a non-implantable and reusable tensioner, such as the one described in patent EP 3.200.710 B1, possibly in combination with the pre-tensioner described in patent FR 3.026.635 A1, or the non-implantable, and in particular disposable, tensioner, such as the one described in the application WO 2018/202839 A1.

The present disclosure relates, according to a fifth aspect, to a strapping device, in particular for the consolidation of a periprosthetic fracture, comprising:
- an elongate hollow textile element comprising an attachment portion and an adjustable loop, whose perimeter is adjustable by sliding a portion of the adjustable loop in an interior volume of a sleeve arranged in the textile element, and
- a strapping closing member configured so as to be secured to the adjustable loop and the attachment portion, and
- an annular member at least partly formed in the elongate hollow textile element, the free end of the elongate element being configured to pass through said annular member, and in that the strapping device comprises a clamping position of the strapping, in which a traction on a free end of the elongate element, passing through the annular member, in a first direction causes the sliding of the adjustable loop portion in the interior volume of the sleeve and correlatively the reduction of the perimeter of the adjustable loop, and a locking position in which the sliding of the adjustable loop is prevented when a traction is exerted on the adjustable loop in a second direction, opposite to the first direction.

The annular member is preferably as described according to any one of the examples described (in particular 1 to 17) with reference to the first aspect of the disclosure.

The strapping closing member is preferably as described according to any one of the examples described (in particular 1 to 17) with reference to the first aspect of the disclosure.

In general, the examples according to the first aspect of the disclosure, in particular the examples from one to seventeen, and/or the definitions and/or example(s) with reference to the first aspect of the disclosure can be combined independently of each other, with the strapping device according to the fifth aspect of the disclosure.

The first, second, third, fourth and fifth aspects of the disclosure can be combined together, and this independently of each other.

DESCRIPTION OF THE DRAWINGS

The disclosure will be better understood upon reading the following description of one embodiment of the disclosure given by way of non-limiting example, with reference to the appended drawings, in which.

DETAILED DESCRIPTION

FIGS. 1 to 5 schematically represent different examples of strapping closing members according to the disclosure.

Figure 1:
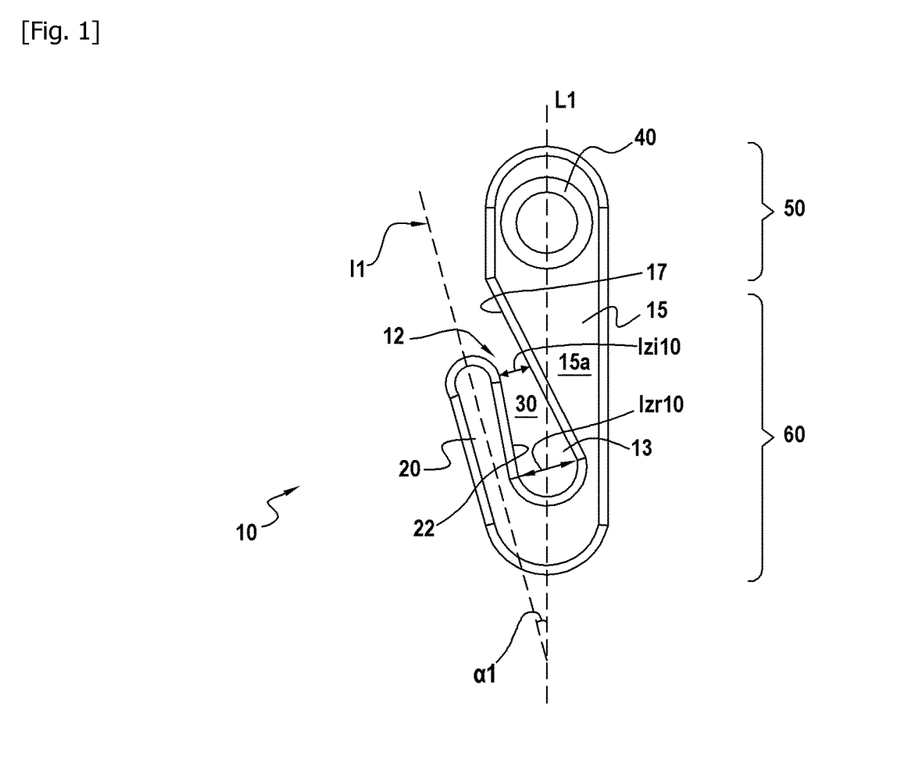
FIG. 1 schematically illustrates a top view of a first example of a closing member according to the disclosure.

The closing member 10 comprises a main branch 15 having a longitudinal axis L1, and an auxiliary branch 20 having a longitudinal axis l1, projecting from said main branch 15. The axes L1 and l1 are secant and form together an angle alpha1, particularly less than or equal to 45°, in particular less than or equal to 30°. The auxiliary branch 20 comprises an inner side wall 22 and the main branch 15 comprises a first inner side wall 17. The inner side walls 17 and 22 face each other and open out into the U-shaped housing 30. The U-shaped housing 30 comprises an introduction area 12 having a width lzi10, and a receiving area 13 having a width lzr10 formed in the groove of the U. The width lzi10 is smaller than the width lzr10, and lzi10 is smaller than the outer diameter of the elongate element with which it cooperates. Thus, once a portion of the elongate element has been forcefully placed in the receiving area 13, it is retained in the groove of the U-shaped housing 30 by the introduction area 12. The closing member 10 also comprises a through opening 40 extending between the upper 15a and lower walls of the main branch 15. As seen in FIG. 1, the upper 15a and lower walls of the main branch 15 are in planes substantially parallel to each other, and secant, in particular substantially perpendicular, to the plane comprising the first inner side wall 17. The closing member 10 comprises a front part 50, which comprises the through opening 40, and a rear part 60, which comprises the U-shaped housing.

The closing members 100, 200, 300 and 400 will be described below by their difference(s) with the closing member 10.

Figure 2:
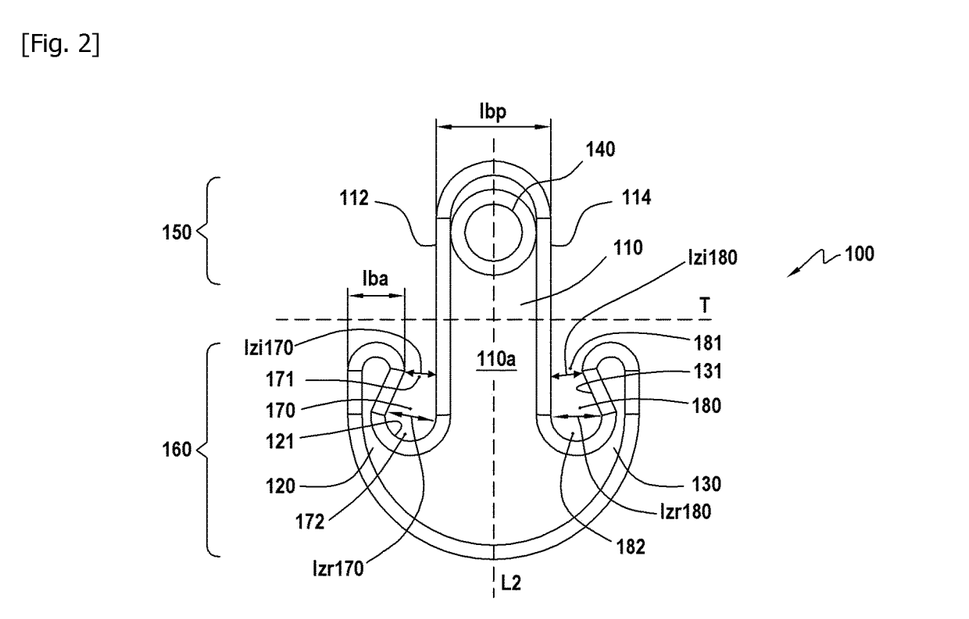
FIG. 2 schematically illustrates a top view of a second example of a closing member according to the disclosure.

The closing member 100 of FIG. 2 comprises a main branch 110, a first auxiliary branch 120 and a second auxiliary branch 130. The auxiliary branches 120, 130 project on either side of the main branch 110 that is to say on either side of its longitudinal axis L2. The closing member 100 comprises a front part 150 comprising a through opening 140 and a rear part 160 comprising the auxiliary branches 120 and 130, delimiting with the main branch 110, a first U-shaped housing 170, and a second U-shaped housing 180. The first auxiliary branch 120 comprises an inner side wall 121 and the second auxiliary branch 130 comprises an inner side wall 131. The U-shaped housings 170 and 180 each comprise an introduction area 171, 181 whose size, lzi170 and lzi180 respectively, is smaller than the size, lzr170 and lzr180, of the receiving areas 172, 182. lzi 170 and lzi 180 are the distance between the side walls 121 and 112 in the introduction area 171 or 181 respectively. lzr170 and lzr180 are each the distance between the side walls 114 and 131 in the receiving area 172 or 182 respectively. The main branch 110 comprises a first inner side wall 112 and a second inner side wall 114. The first U-shaped housing 170 is thus at least partly delimited by the inner side walls 121 and 112, while the second U-shaped housing 180 is at least partly delimited between the inner side walls 131 and 114. The through opening 140 extends between the upper wall 110a and the lower wall (not shown) of the main branch 110.

Figure 3:
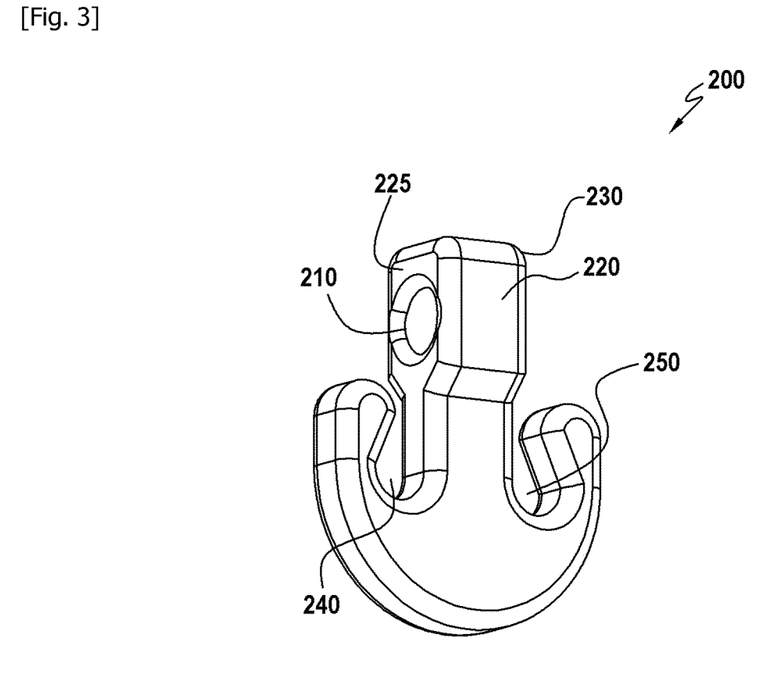
FIG. 3 schematically represents a perspective view of a third example of a closing member according to the disclosure.

The closing member 200 is similar to the closing member 100. The closing member 200 comprises a through opening 210 disposed in the main branch 220. The through opening 210 extends between a first inner side face 225 of the main branch 210, and a second inner side face 230 of the main branch 210. When the adjustable loop according to the disclosure is passed for example around the main branch 210, and is housed in the hollows of the first 240 and second 250 U-shaped housings, the attachment portion passed through the through opening 210 is disposed in a plane substantially perpendicular to the plane comprising the adjustable loop portion passed around the main branch 220. In the case of the closing member 100, the attachment portion passed in the through opening 140, and the adjustable loop passed in the first 170 and second 180 housings, are substantially in a parallel plane. The different positions of the through opening thus making it possible to orient differently the parts of the elongate element secured thereto.

Figure 4:
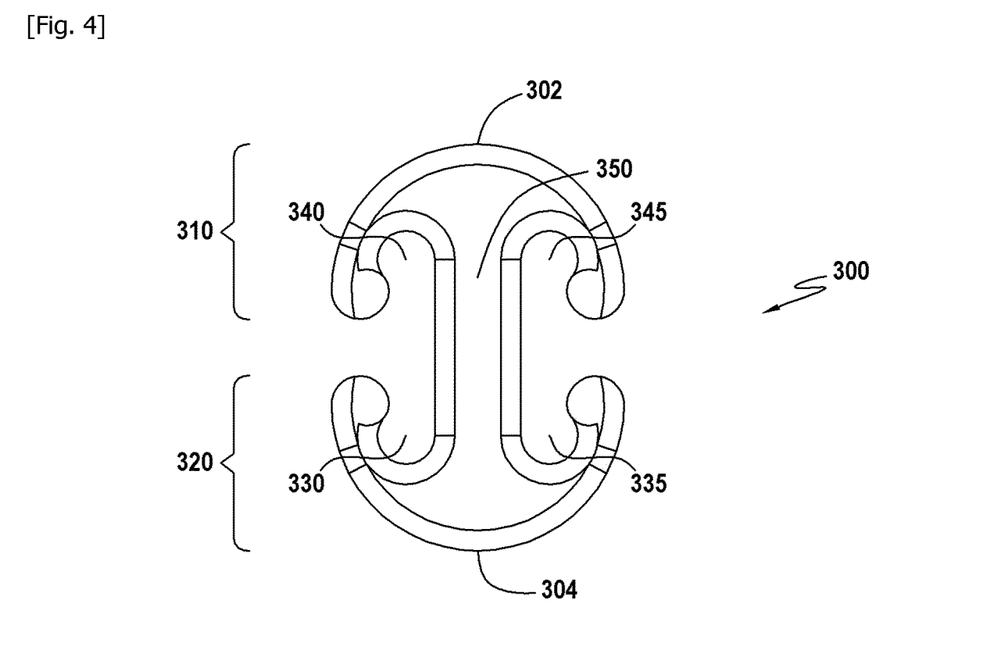
FIG. 4 schematically represents a top view of a fourth example of a closing member according to the disclosure.

The closing member 300 comprises a front part 310 and a rear part 320 similar in that they each comprise two U-shaped housings, themselves equivalent to the two housings 170, 180 of the closing member 100 or to the two housings 240 and 250 of the closing member 200. The closing member 300 thus comprises first 330, second 335, third 340 and fourth 345 U-shaped housings. The front part 310 and the rear part 320 thus each have an anchor shape, in particular whose upper edge 302 and lower edge 304 are rounded. When using the closing member 300, the attachment portion is preferably an attachment loop which can be passed around the main branch 350, and engaged with the U-shaped housings 340, 350 in the front part 310, or the U-shaped housings 330, 335 in the rear part.

Figure 5:
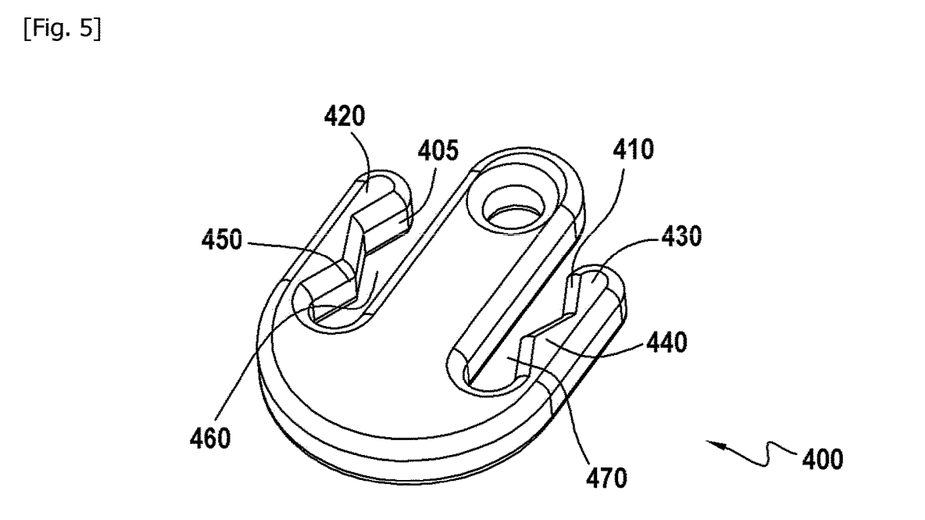
FIG. 5 schematically represents a perspective view of a fifth example of a closing member according to the disclosure.

The closing member 400 represented in FIG. 5 is equivalent to the closing member 100 except that the inner side walls 405 and 410, respectively, of the first 420 and second 430 auxiliary branches each comprise a projection 450 and 440, respectively. The projections 440, 450 project into the first 460 and second 470 U-shaped housings and thus increase the contact surface with the parts of elongate elements received therein. This disposition allows improving the holding of the elongate element parts disposed in the receiving areas of the U-shaped housings 460, 470.

Figure 6:
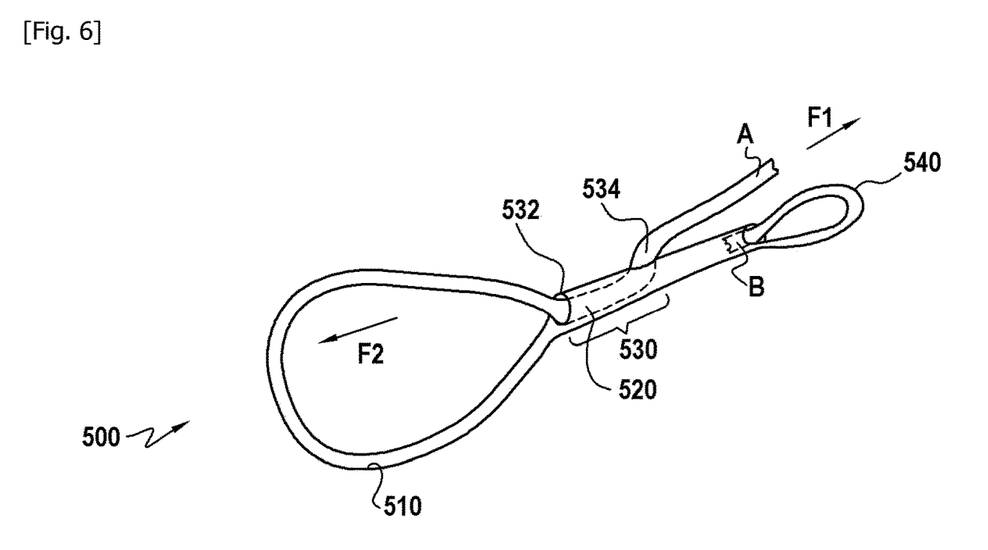
FIG. 6 schematically illustrates a perspective view of a first example of an elongate textile element according to the disclosure.

FIG. 6 represents an example of an elongate hollow textile element 500 according to the disclosure, having a free end A, and a second free end B secured to the elongate element 500, for example by means of a splice. The elongate element 500 comprises an adjustable loop 510 whose perimeter is adjustable by sliding of a portion 520 of the adjustable loop in an interior volume of a sleeve 530 arranged in said elongate element 500. The sleeve 530 comprises an inlet orifice 532 and an outlet orifice 534. The free end A is retracted into the sleeve 530 through the inlet orifice 532, then deployed through the outlet orifice 534. The free end B is folded back on itself and retracted into the interior volume of the elongate element 500 and thus forms an attachment loop 540.

Figure 7:
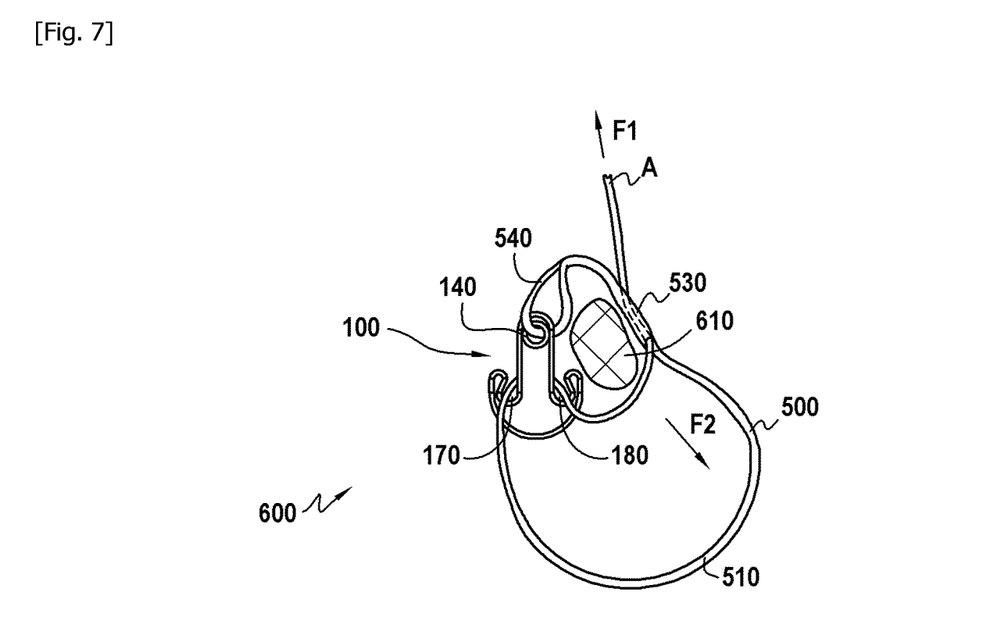
FIG. 7 schematically illustrates a first example of a strapping device according to the disclosure in a first strapping closing configuration.

FIG. 7 represents an example of a strapping device 600 according to the disclosure comprising the elongate element 500 and the closing member 100. The elongate element 500 is disposed around the bone structure 610 to be circled. The attachment loop 540 is disposed in the through opening 140, the splice for securing the free end B is thus preferably performed after the passage of the free end B through the opening 140. The adjustable loop 510 is thus passed behind the bone structure 610 to be treated, in particular using a wire guide, then the adjustable loop 510 is disposed around the main branch 110, and housed in the receiving areas 172 and 182, respectively, of the housings 170 and 180. Then, traction is exerted on the free end A in a direction F1, that is to say a direction opposite to the inlet orifice 534, so as to allow the sliding of the adjustable loop 510 on itself and correlatively the clamping of the strapping. The free end A can be tensioned using a mechanical (in particular non-implantable) tensioner. When the tensile force is no longer applied, the portion of the adjustable loop 510 disposed in the sleeve 530 is prevented from sliding by the sleeve 530. The inner surface of the sleeve 530 thus comes into contact with the outer surface of the elongate element 500 portion 520 disposed therein, the friction between said surfaces locking the sliding. It is possible to loosen the strapping, by bringing the inlet 532 and outlet 534 orifices closer to each other and by holding the sleeve, then by pulling on the adjustable loop 510 in a direction F2, opposite to the direction F1, in particular to the outlet orifice 534. The bone structure 610 is thus perfectly circled by the elongate element 500 applying significant compression, and adjustable for the surgeon due to the clamping sleeve 530. It is thus possible to have several strapping devices during an intervention and to adjust in a differentiated manner, reversibly, the clamping of each of the strappings.

Figure 8:
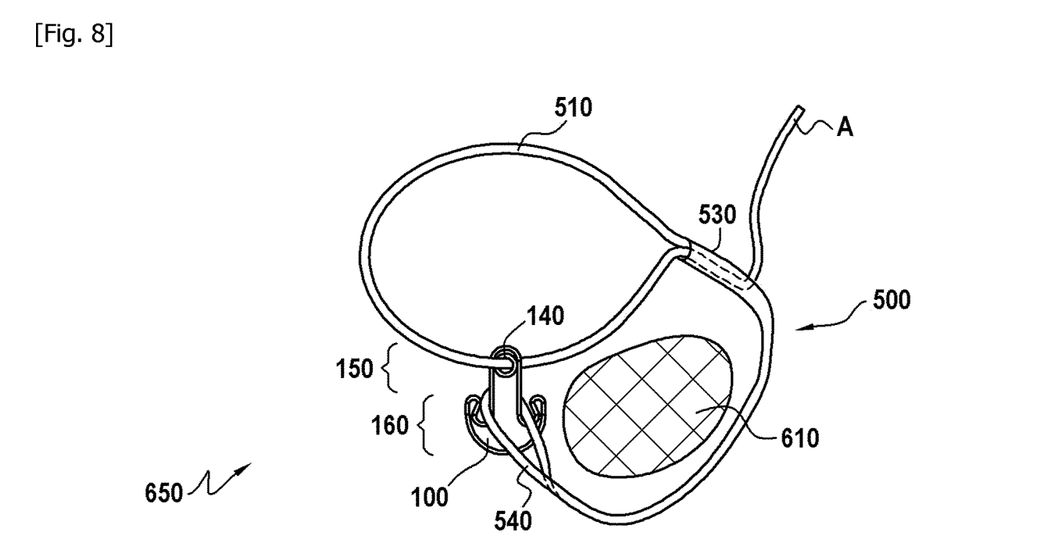
FIG. 8 schematically illustrates the first example of a strapping device of FIG. 7 in a second strapping closing configuration.
Figure 9:
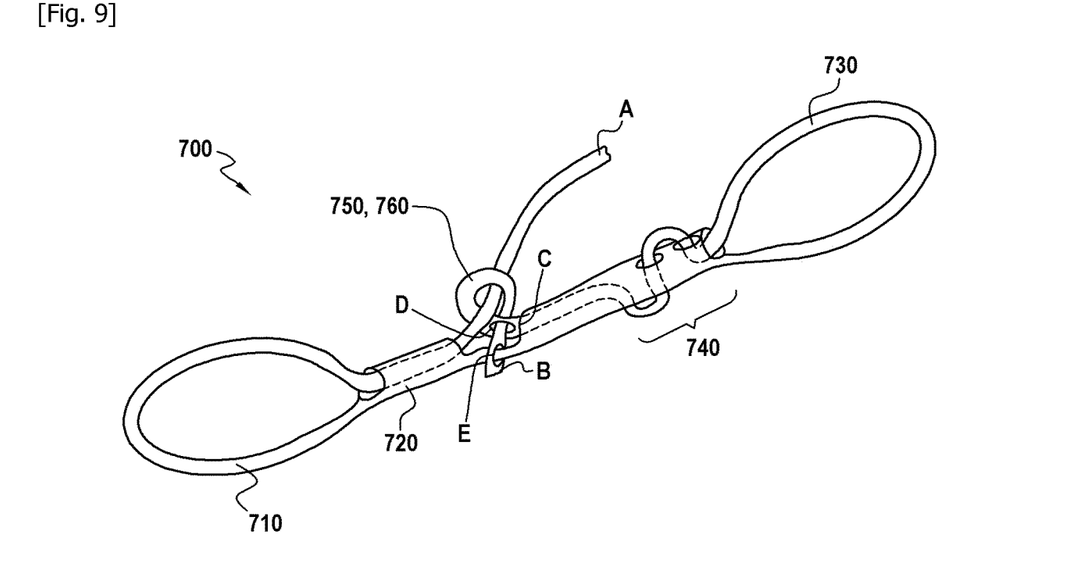
FIG. 9 schematically illustrates a perspective view of a second example of an elongate textile element according to the invention.

In the implantation position represented in FIG. 7, the attachment loop 540 is secured to the through opening 140. It is possible to provide that the attachment loop 540 is secured to the closing member 100 as represented for the strapping device 650 in FIG. 8. The attachment loop 540 is secured to the rear part of the closing member 100 in an equivalent manner to the adjustable loop 510 represented in FIG. 7. The adjustable loop 510 in FIG. 8 is secured to the through opening 140. In this case, the manufacture of the sleeve 530 in the elongate textile element 500 can be performed after the passage of the free end A in the through opening 140. FIG. 9 represents another example of an elongate element 700 according to the invention. The elongate element 700 comprises an adjustable loop 710 whose perimeter is adjustable by sliding of a portion of the adjustable loop 710 in an interior volume of a sleeve 720 arranged in said elongate element 700. The elongate element 700 also comprises an attachment loop 730 formed by repeated insertion of the free end B through the elongate element 700 according to a securing area 740. These multiple insertions are an example of a splice for the securing of a portion of the elongate element 700 in the vicinity of the free end B to the base of the attachment loop 730. The free end B then emerges from the interior volume of the elongate element 700 at the exit point C, then is folded back on itself even so as to form a loop 750, then passed through two portions of the elongate element 500 at the point D, and is then secured to the elongate element along a securing area E. The loop 750 forms an annular member 760 through which the free end A is passed.

Figure 10:
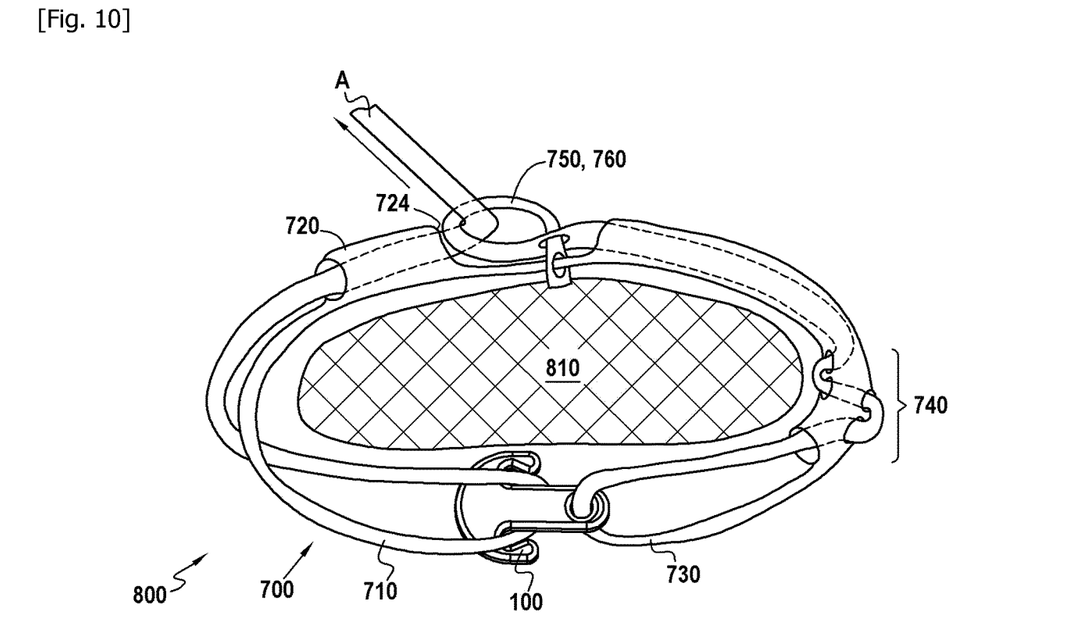
FIG. 10 illustrates a second example of a strapping device according to the disclosure in the first strapping closing configuration.

In operation, as represented in FIG. 10, the strapping device 800 comprises the elongate element 700, and for example the closing member 100. The operation of the elongate element 700 for the clamping of the strapping around the bone structure 810 and its reversible locking via the sleeve 720 are similar to the behavior of the elongate element 500. During clamping, the free end A does not exert a shear force on the sleeve, particularly at its outlet orifice 724. This disposition thus advantageously allows applying tensile forces on the free end A greater than those applied on the elongate element 500. In addition, the annular member 760 is formed from the free end B, which is secured in a securing area E to a portion of the elongate element 500 disposed between the sleeve 720 and the attachment loop 740, which allows transmitting the tensile stress to the entire elongate element 500. The compression applied on the bone structure 810 is thus homogeneous and significant, promoting high-quality osteosynthesis.

The invention claimed is:

1. A strapping device comprising:
   an elongate hollow textile element comprising an attachment portion and an adjustable loop, wherein a perimeter of the adjustable loop is adjustable by sliding a portion of the adjustable loop in an interior volume of a sleeve arranged in the elongate hollow textile element, and
   a strapping closing member comprising:
     a front part to which the adjustable loop or the attachment portion is connected, and
     a rear part comprising a first U-shaped housing configured to receive part of the attachment portion or the adjustable loop, and
   wherein the strapping device further comprises a clamping position of the strapping device, in which traction on a first free end of the elongate hollow textile element in a first direction causes the sliding of the adjustable loop portion in the interior volume of the sleeve and correlatively a reduction in the perimeter of the adjustable loop, and a locking position in which the sliding of the adjustable loop is prevented when traction is exerted on the adjustable loop in a second direction opposite to the first direction, and
     wherein the strapping device further comprising an annular member, the first free end of the elongate hollow textile element being configured to pass through the annular member, and wherein the annular member is at least partly formed in the elongate hollow textile element,
     wherein the annular member comprises a second free end of the elongate hollow textile element passed through at least two wall portions of the elongate hollow textile element by passing through the interior volume of the elongate hollow textile element so as to form a loop through which the first free end of the elongate hollow textile element passes, said two wall portions of the elongate hollow textile element being substantially opposite.

2. The strapping device of claim 1, wherein the strapping closing member comprises a first auxiliary branch and a main branch at least partly delimiting the first U-shaped housing.

3. The strapping device of claim 2, wherein the adjustable loop, or the attachment portion is a loop that is passed around the main branch.

4. The strapping device of claim 1, wherein in the locking position, the sliding of the adjustable loop is prevented by the sleeve which is a member for locking the sliding of the adjustable loop portion disposed in the interior volume of the sleeve.

5. The strapping device of claim 2, wherein the strapping closing member comprises a second U-shaped housing configured to receive part of the attachment portion or of the adjustable loop.

6. The strapping device according to claim 5, wherein the strapping closing member comprises a second auxiliary branch, and the main branch and the second auxiliary branch partly delimit the second housing.

7. The strapping device of claim 5, wherein the rear part or the front part comprises the second housing.

8. The strapping device of claim 7, wherein the front part or the rear part comprises a third U-shaped housing, and optionally a fourth U-shaped housing.

9. The strapping device of claim 1, wherein the front part of the strapping closing member has the general shape of an anchor.

10. The strapping device of claim 1, wherein the annular member is secured to a portion of the elongate hollow textile element disposed between, and in the extension of, the sleeve and the attachment portion.

11. The strapping device of claim 1, wherein the first U-shaped housing comprises at least one side wall comprising at least one projection projecting into the housing.

12. The strapping device of claim 2, wherein the front part comprises a through opening and through which the adjustable loop or the attachment portion is passed.

13. The strapping device of claim 12, wherein the through opening extends between and opens out onto two side walls of the main branch.

14. The strapping device of claim 12, wherein the through opening extends between and opens out onto upper and lower walls of the main branch.

15. The strapping device of claim 1, wherein the strapping closing member comprises an anchoring stud and the attachment portion is anchored to the anchoring stud.

16. The strapping device of claim 1, wherein the elongate hollow textile element is a braid.

17. An implantable osteosynthesis strapping device, comprising an implantable strapping and a reinforcing plate and at least one strapping for securing the reinforcing plate, configured to allow the securing of the plate to at least one bone portion.

18. A kit for the use of an osteosynthesis strapping device, comprising an osteosynthesis strapping or an implantable strapping, and a tensioner.

19. An implantable strapping device, comprising:

an elongate hollow textile element comprising an attachment portion and an adjustable loop, wherein a perimeter of the adjustable loop is adjustable by sliding a portion of the adjustable loop in an interior volume of a sleeve arranged in the elongate hollow textile element, and a strapping closing member configured so as to be secured to the adjustable loop and the attachment portion, and an annular member at least partly formed in the elongate hollow textile element, a first free end of the elongate hollow textile element is configured to pass through said annular member, and wherein the strapping device further comprises a strapping clamping position in which a traction on the first free end of the elongate hollow textile element, passing through the annular member, in a first direction causes the sliding of the adjustable loop portion in the interior volume of the sleeve and correlatively a reduction of the perimeter of the adjustable loop, and a locking position in which the sliding of the adjustable loop is prevented when a traction is exerted on the adjustable loop in a second direction, opposite to the first direction, and wherein the annular member comprises a second free end of the elongate hollow textile element passed through at least two wall portions of the elongate hollow textile element by passing through the interior volume of the elongate hollow textile element so as to form a loop through which the first free end of the elongate hollow textile element passes, said two wall portions of the elongate hollow textile element being substantially opposite.

20. The strapping device of claim 1, wherein the diameter of the annular member is not adjustable.

* * * * *